(12) United States Patent
Yang et al.

(10) Patent No.: US 7,060,034 B1
(45) Date of Patent: Jun. 13, 2006

(54) TUNNEL TYPE ELECTRONIC SPHYGMOMANOMETER MEASURING UNIT ASSEMBLY

(75) Inventors: Paul Yang, Chung Ho (TW); Pin-Hsuan Hung, Chung Ho (TW)

(73) Assignee: Health & Life Co., Ltd., Chung Ho (TW)

( * ) Notice: Subject to any disclaimer, the term of this patent is extended or adjusted under 35 U.S.C. 154(b) by 0 days.

(21) Appl. No.: 11/079,283

(22) Filed: Mar. 15, 2005

(51) Int. Cl.
*A61B 5/00* (2006.01)

(52) U.S. Cl. .................. 600/490; 600/493; 600/499; 600/500

(58) Field of Classification Search ............... None
See application file for complete search history.

(56) References Cited

U.S. PATENT DOCUMENTS

| | | | | |
|---|---|---|---|---|
| 5,218,966 A | * | 6/1993 | Yamasawa | ............ 600/490 |
| 6,428,124 B1 | * | 8/2002 | Bluth et al. | .............. 312/194 |
| 2002/0095091 A1 | * | 7/2002 | Che et al. | ............... 600/490 |
| 2003/0220575 A1 | * | 11/2003 | Fumuro et al. | .......... 600/500 |
| 2005/0033187 A1 | * | 2/2005 | Itonaga et al. | ........... 600/485 |
| 2005/0192501 A1 | * | 9/2005 | Sano et al. | .............. 600/499 |

* cited by examiner

*Primary Examiner*—Robert L. Nasser
(74) *Attorney, Agent, or Firm*—Bacon & Thomas, PLLC

(57) ABSTRACT

The present invention discloses a tunnel type electronic sphygmomanometer measuring unit assembly that mainly improves the assembly between a measuring unit of a tunnel type electronic sphygmomanometer and a tunnel type electronic sphygmomanometer body of a prior art by installing an axle unit between the measuring unit of tunnel type electronic sphygmomanometer and the tunnel type electronic sphygmomanometer body to provide a multidirectional rotary function, such that the sphygmomanometer can be rotated in different directions by means of the axle unit to fit the posture of a user when a blood pressure is measured, and thus the invention enhances the accuracy of the sphygmomanometer for measuring blood pressure.

1 Claim, 5 Drawing Sheets

TUNNEL TYPE ELECTRONIC SPHYGMOMANOMETER MEASURING UNIT ASSEMBLY

BACKGROUND OF THE INVENTION

1. Field of the Invention

The present invention relates to a tunnel type electronic sphygmomanometer measuring unit assembly, and more particularly to a multidirectional rotary assembly of a measuring unit of an electronic sphygmomanometer that is applied to the position of a user's arm for measuring blood pressure.

2. Description of the Related Art

Referring to FIG. 1, a conventional tunnel type electronic sphygmomanometer for measuring blood pressure at the position of an arm is illustrated. The conventional tunnel type electronic sphygmomanometer 10 comprises: a sphygmomanometer body 100 and a measuring unit 200, and the measuring unit 200 is a cylinder that allows a user's arm to pass through, and the measuring unit 200 is pivotally coupled to the sphygmomanometer body 100 by a hinge 201.

Since the size of the arm of different people is different and the posture of a user when using the sphygmomanometer varies, the accuracy of the measurement will be affected. For example, the influence on measurement caused by the posture is described as follows. If the measuring position is higher than the position of the user's heart, the blood pressure will be decreased by approximately 8 mm Hg for every 10 cm higher; and if the measuring position is lower than the position of the user's heart, the blood pressure will be increased by approximately 8 mm Hg for every 10 cm lower. Therefore, the conventional prior measuring unit and sphygmomanometer body can only provide an assembly with linear movement. In other word, the conventional prior measuring unit and sphygmomanometer body can only be moved to the front or to the back, but cannot be turned to the left or the right to accommodate different postures of a user, and thus making the user uncomfortable and causing inaccurate measurements.

SUMMARY OF THE INVENTION

In view of the foregoing shortcomings of the prior art, the inventor of the present invention invented a tunnel type electronic sphygmomanometer measuring unit assembly by installing a multidirectional axle unit between the measuring unit for measuring blood pressure at the position of a user's arm and the tunnel type electronic sphygmomanometer body to improve the adaptability and convenience for users and enhance the accuracy of the measurement and the comfort of users.

Therefore, it is a primary objective of the present invention to provide a tunnel type electronic sphygmomanometer having a multidirectional axle unit to be applied at the position of a user's arm for measuring blood pressure so as to give a more accurate measurement.

To achieve the foregoing objective, the present invention discloses a tunnel type electronic sphygmomanometer measuring unit assembly, which comprises: a tunnel type electronic sphygmomanometer body, and the tunnel type electronic sphygmomanometer body has a pump, a data processing storage unit, and a display unit, etc; a measuring unit, being pivotally coupled to the foregoing tunnel type electronic sphygmomanometer body by a multidirectional axle unit for measuring the signals of blood circulation system including the blood pressure, heartbeat and pulse of a user, and the data of the blood circulation system including the blood pressure, heartbeat and pulse are displayed on the display unit for user's record and observation.

BRIEF DESCRIPTION OF THE DRAWINGS

The above objects, features and advantages of the present invention will become apparent from the following detailed description taken with the accompanying drawing.

DETAILED DESCRIPTION OF THE PREFERRED EMBODIMENTS

Figure 1:
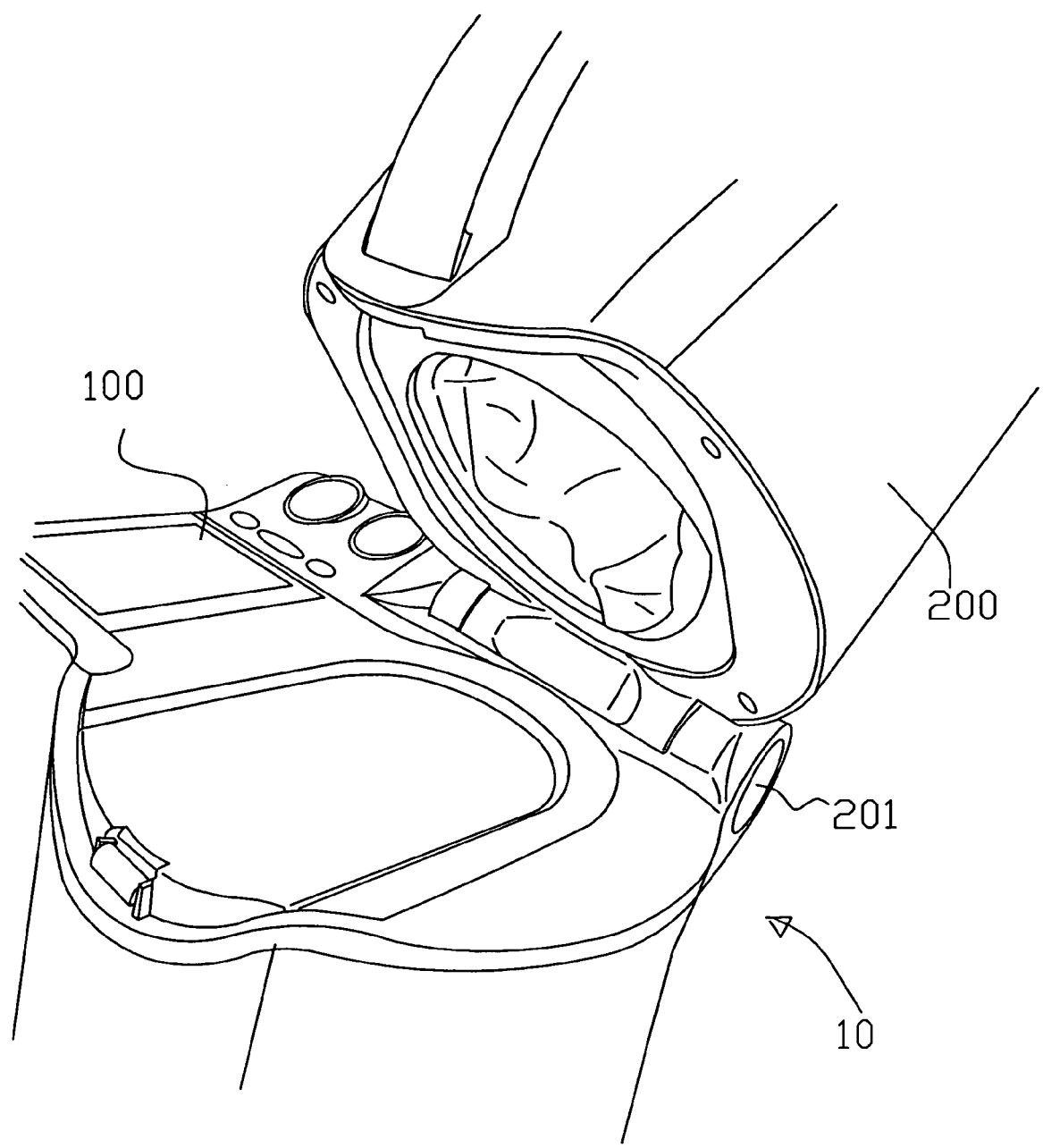
FIG. 1 is a perspective view of a conventional prior tunnel type electronic sphygmomanometer.
Figure 2:
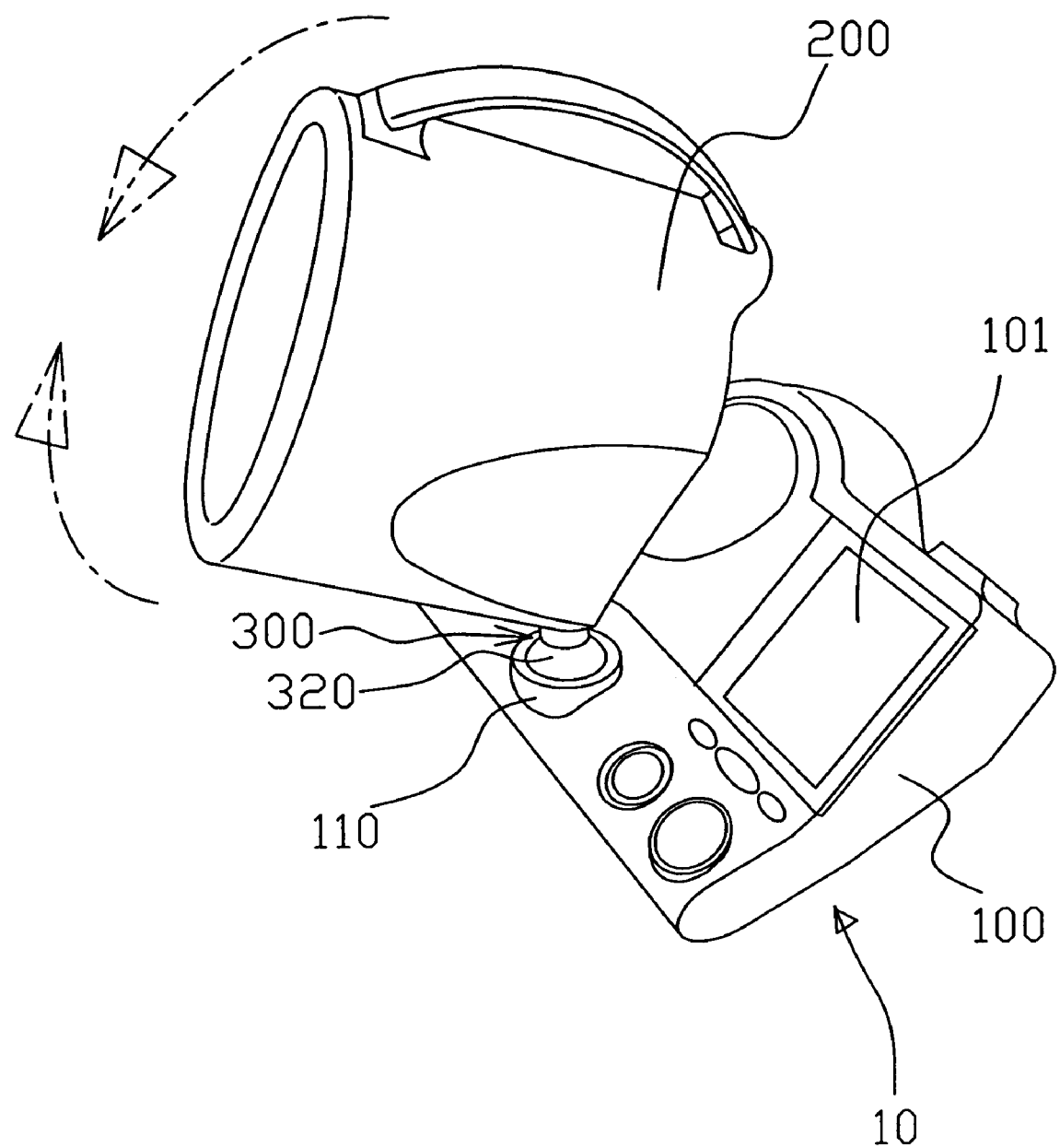
FIG. 2 is a perspective view of the tunnel type electronic sphygmomanometer measuring unit assembly according to a preferred embodiment of the present invention.
Figure 3:
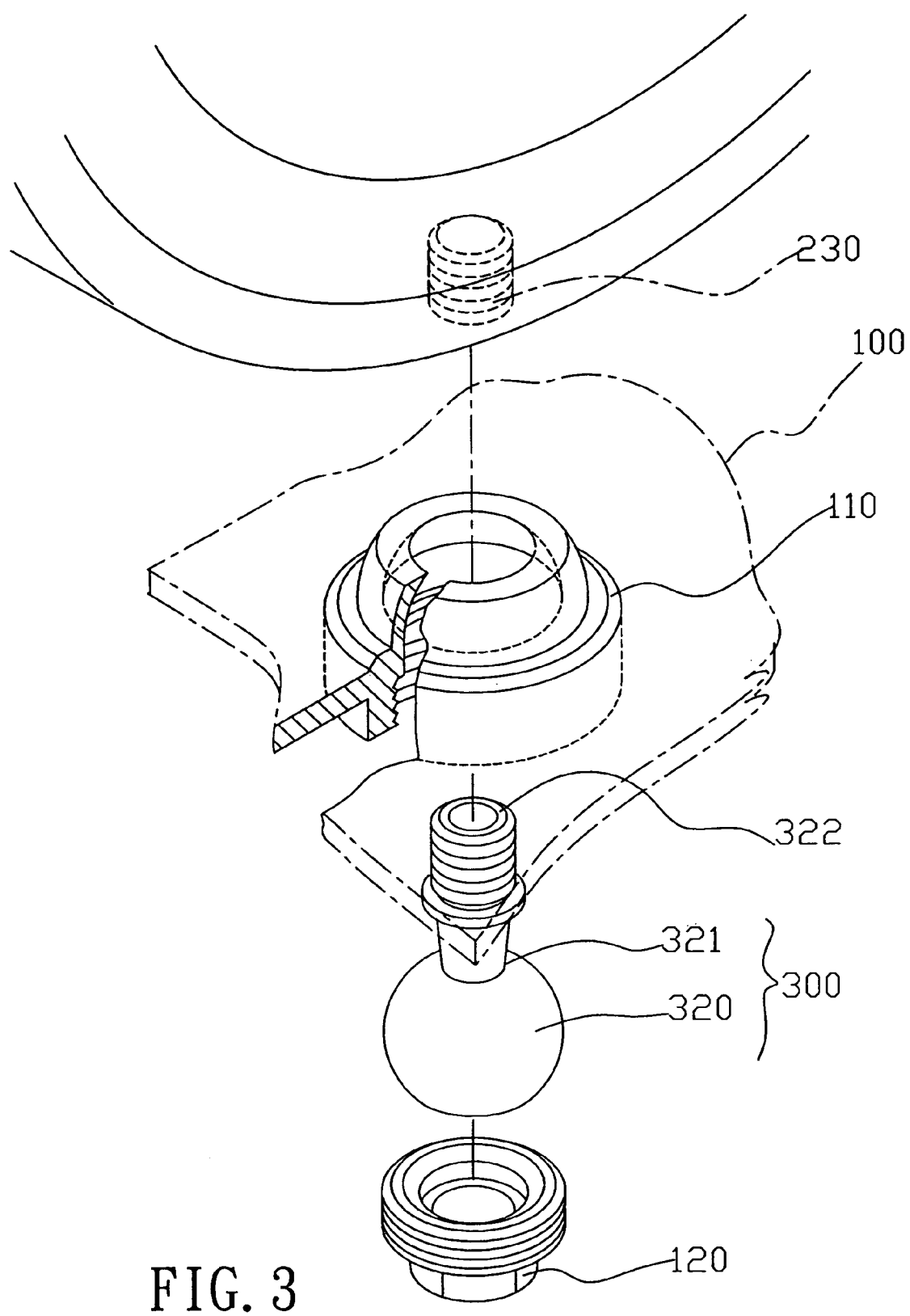
FIG. 3 is an exploded view of the axle unit according to a preferred embodiment of the present invention.
Figure 4:
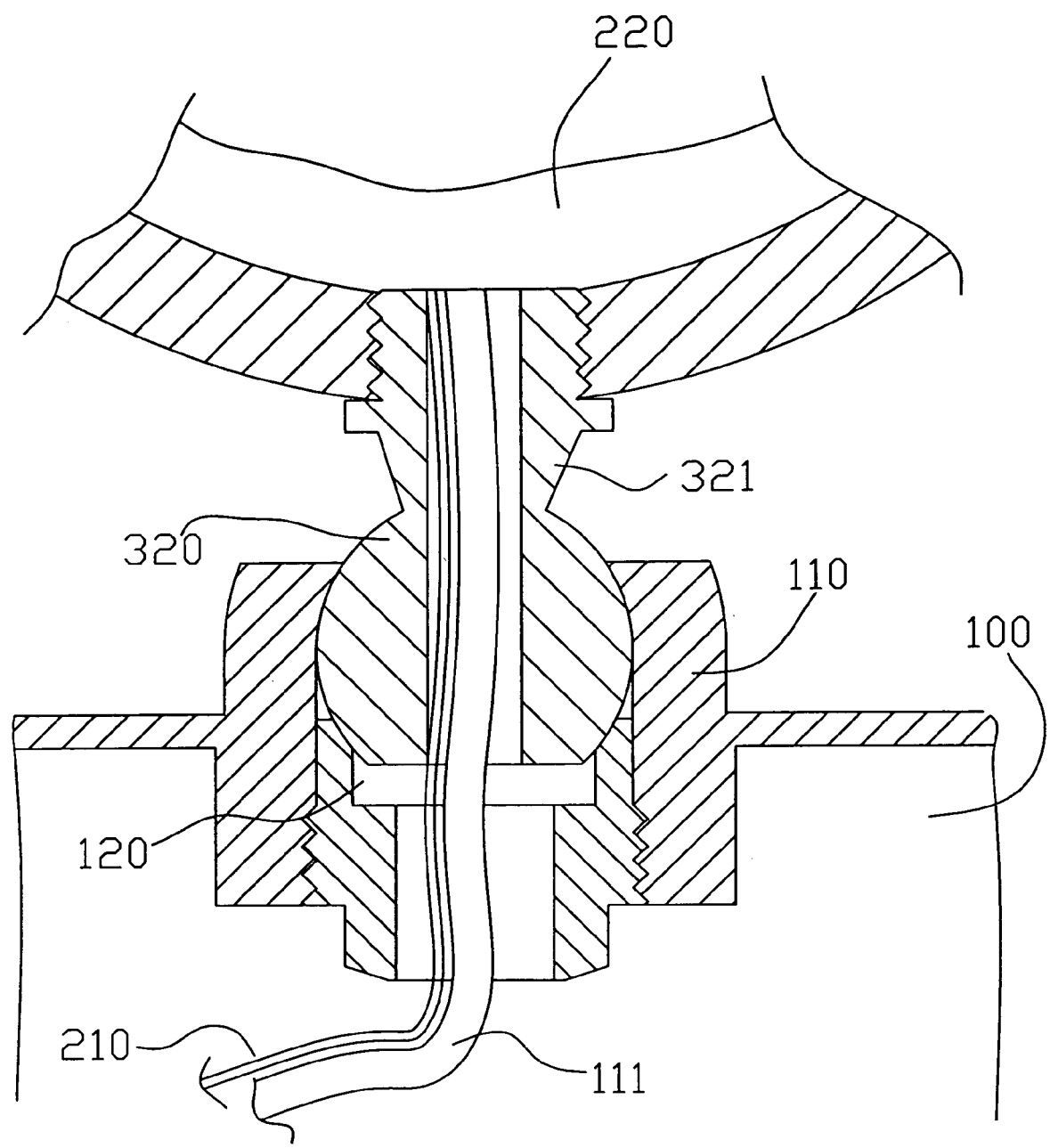
FIG. 4 is a cross-sectional view of the axle unit according to a preferred embodiment of the present invention.

Referring to FIGS. 2, 3 and 4, a tunnel type electronic sphygmomanometer according to a preferred embodiment of the present invention comprises:

- a tunnel type electronic sphygmomanometer body 100, having a pump (not shown in the figure) disposed therein, and the pump includes an air duct 111;
- a data processing storage unit (not shown in the figure), for processing and storing the measured blood pressure, heartbeat, and pulse signals;
- a measuring unit 200, which is a cylinder for allowing a user's arm to pass through, and the measuring unit 200 is pivotally coupled to the tunnel type electronic sphygmomanometer body 100 by an axle unit 300 having a multidirectional rotary function for measuring the blood circulation signals including the blood pressure, heartbeat and pulse of a user, and these signals are connected to the tunnel type electronic sphygmomanometer body 100, and the measuring unit 200 has a signal transmission unit 210 connected to the tunnel type electronic sphygmomanometer body 100 and the measuring unit 200 has an air cuff 200 disposed thereon and coupled to the air duct 111;
- an axle unit 300 (refer to FIGS. 3 and 4), for pivotally connecting the tunnel type electronic sphygmomanometer body 100 and the measuring unit 200, and the axle unit comprises a ball axle 320, and ball axle 320 forms a hollow passage disposed therein, and a neck section 321 and a lock section 322 are extended from an end of the ball axle 320, and the bottom of the ball axle 320 presses on a retaining base 120, and the lock end 322 is secured into a screw hole 230 of the measuring unit 200. When the measuring unit 200 is turned, the neck section 321 presses on a sleeve section 110 for a limit control, and the ball axle 320 rotates within the sleeve section 110.

Figure 5:
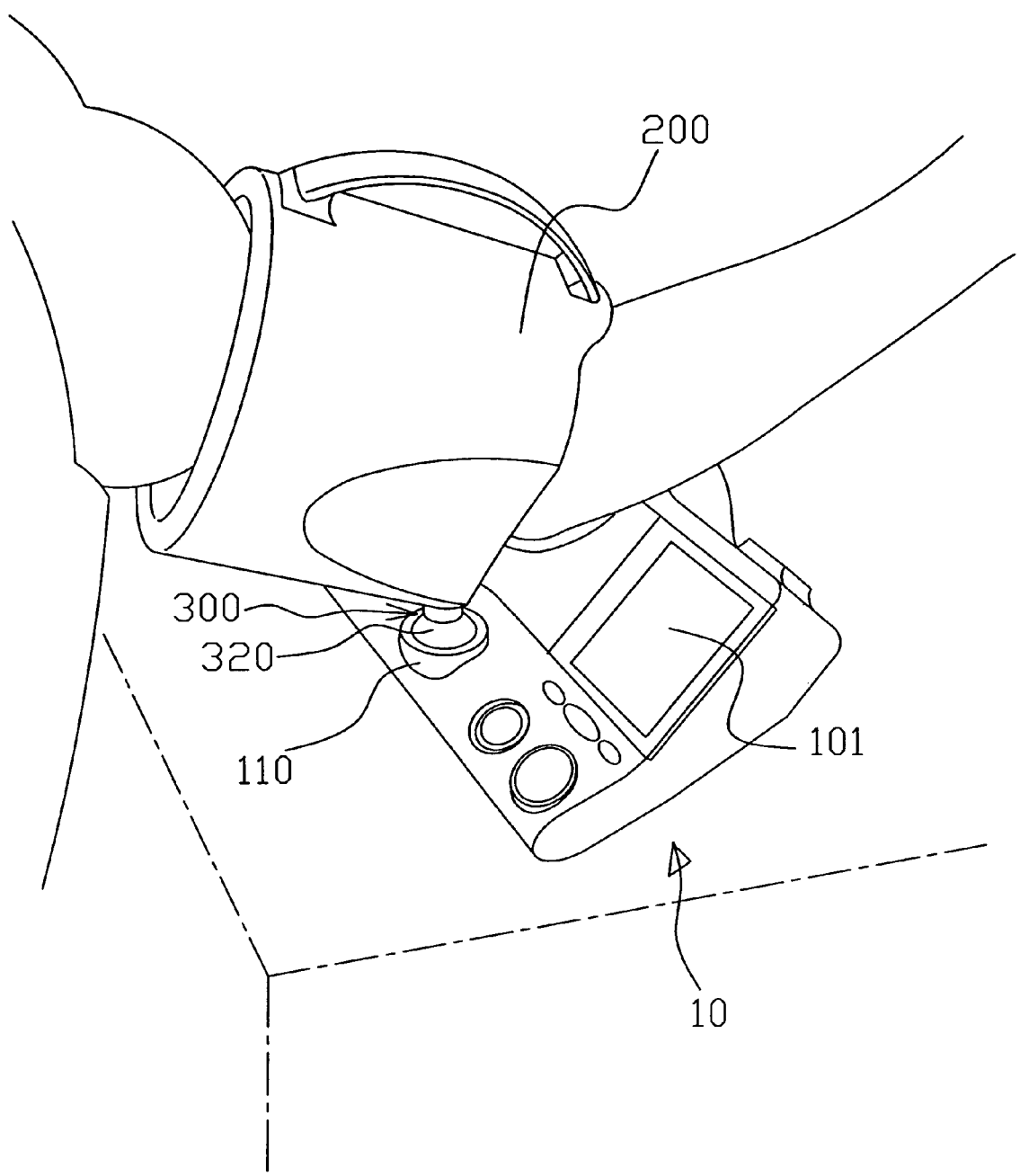
FIG. 5 is a schematic view of the present invention when it is in use.

Referring to FIG. 5, when the present invention is in use, a user passes an arm into the measuring unit 200, and the measuring unit 200 can be selectively turned by a user to an appropriate angle through the axle unit 300, and air is pumped into the air cuff 220 for the measurement by the pump and the air duct 111. The measured blood pressure signals are sent to the tunnel type electronic sphygmomanometer body 100 by a signal transmission unit 210. After the tunnel type electronic sphygmomanometer body 100 receives the data, the data processing storage unit (not shown in the figure) will output the signals to the display unit 101.

Therefore, before a user passes an arm into the cylinder for measuring a blood pressure, the user can turn the measuring unit 200 to an appropriate and comfortable angle or position first. The tunnel type electronic sphygmomanometer measuring unit assembly is no longer restricted by the positions of being moved linearly to the front or the rear, and thus can perform the blood pressure measurement at a comfortable is posture and improve the accuracy of the measured signals. After its use, the measuring unit 200 can be folded towards the tunnel type electronic sphygmomanometer body 100 to reduce the overall volume for its storage.

In summation of the above description, the present invention herein enhances the performance than the conventional structure and further complies with the patent application requirements and is submitted to the Patent and Trademark Office for review and granting of the commensurate patent rights.

While the invention has been described by way of examples and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A tunnel type electronic sphygmomanometer measuring unit assembly, comprises:
    a tunnel type electronic sphygmomanometer body;
    an axle unit having a ball axle said ball axle forming a hollow passage disposed in the axle; and
    a measuring unit;
    wherein said measuring unit is a cylinder arranged to receive a user's arm,
    wherein a signal transmission unit and an air cuff are disposed in the measuring unit, and
    wherein said measuring unit is pivotally coupled to said tunnel type electronic sphygmomanometer body by said axle unit, such that said measuring unit can be rotated on all sides to different angles to (a) fit a comfortable position of a user when a blood pressure is measured and achieve an accurate measurement, and (b) enabling said measuring unit to be folded toward said tunnel type electronic sphygmomanometer body after use to reduce an overall storage volume.

* * * * *